US006436946B1

(12) United States Patent
Mann (10) Patent No.: US 6,436,946 B1
(45) Date of Patent: *Aug. 20, 2002

(54) XANTHINE-CONTAINING COMPOSITIONS FOR ORAL ADMINISTRATION AND USES RELATED THERETO

(76) Inventor: Morris A. Mann, 21669 West 57th Ave., Glendale, AZ (US) 85308

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/087,111

(22) Filed: May 28, 1998

Related U.S. Application Data (63) Continuation-in-part of application No. 09/071,705, filed on May 1, 1998, now abandoned.
(60) Provisional application No. 60/076,114, filed on Feb. 27, 1998, and provisional application No. 60/045,420, filed on May 2, 1997.

(51) Int. Cl.[7] ............................................. A61K 31/195
(52) U.S. Cl. ..................... 514/263; 514/561; 424/752
(58) Field of Search ................. 544/267, 274, 544/263, 561; 514/263, 561; 424/752

(56) References Cited

U.S. PATENT DOCUMENTS

| | | | | | |
|---|---|---|---|---|---|
| 4,390,532 A | * | 6/1983 | Stuttgen et al. | ............... | 514/56 |
| 4,755,517 A | * | 7/1988 | Bruns et al. | ................. | 514/263 |
| 4,775,665 A | * | 10/1988 | Wurtman | ........................ | 54/76 |
| 5,116,605 A | * | 5/1992 | Alt | ............................... | 514/78 |
| 5,292,766 A | * | 3/1994 | Clemens | ...................... | 514/415 |
| 5,373,085 A | * | 12/1994 | Fox et al. | .................... | 528/328 |
| 5,407,684 A | * | 4/1995 | Loria et al. | ................. | 424/442 |
| 5,502,056 A | * | 3/1996 | Breitbarth | .................... | 514/263 |
| 5,527,788 A | * | 6/1996 | Svec et al. | ................... | 514/169 |
| 5,531,993 A | * | 7/1996 | Griat | ........................... | 424/401 |
| 5,543,405 A | * | 8/1996 | Keown et al. | .............. | 514/188 |
| 5,629,002 A | * | 5/1997 | Weuffen et al. | .............. | 424/401 |
| 5,658,576 A | * | 8/1997 | Soudant | ...................... | 424/401 |

OTHER PUBLICATIONS

Seiler, W.G. Akteulle Dermatologie (1981) 7(3): 51–59, English abstract only.*
Seiler et al. Z. Hautkr. (1985) 60(6): 535–36, English abstract only.*
Loriaux et al. Psychopharmacology (1985) 87(4): 390–5.*
Oesterreich et al. Med. Welt (1989) 40(4): 1218–23, English abstract only.*

* cited by examiner

*Primary Examiner*—Jean C. Witz (57) ABSTRACT

There are disclosed compositions for oral administration of a novel pharmaceutical composition, which includes xanthine-based stimulants, various neurotransmitter precursors, minerals, nootropic herbs, and amino acids capable of augmenting the preparation. Also, embodied in these compositions are specific cerebral vasodilators and cognition enhancing neurosteroids.

6 Claims, 4 Drawing Sheets

XANTHINE-CONTAINING COMPOSITIONS FOR ORAL ADMINISTRATION AND USES RELATED THERETO

This application claims the benefit of U.S. Provisional Application No. 60/076,114, filed Feb. 27, 1998 now abandoned; and is a Continuation-In-Part of U.S. application Ser. No. 09/071,705, filed May 1, 1998 now abandoned, which claims the benefit of U.S. Provisional Application No. 60/045,420, filed May 2, 1997 now abandoned.

TECHNICAL FIELD

The present invention relates generally to pharmaceutical compositions and methods for their use, and more specifically to xanthine-containing compositions that enhance cerebral cortical activity, enhance short-term memory, suppress appetite and/or reduce hair loss.

BACKGROUND OF THE INVENTION

The primary effect of all stimulants is to enhance cerebral cortical activity. However, without exception, all stimulants have drawbacks. The primary problems associated with virtually all stimulants are twofold: habituation, and depression when the stimulant is withdrawn. The more powerful the stimulant, the more profound the habituation and/or depression. These problems have been noted with virtually all stimulants that have a primary central nervous system effect. The reason for this problem is that stimulation enhances the metabolism and uptake of the various neurotransmitters and decreases the depolarization time interval. Over time, this leads to prolonged depolarization and depression.

Accordingly, there is a need in the art for pharmaceutical compositions that can increase central nervous system activity without the disadvantages associated with existing stimulants. The present invention fulfills these needs, and provides further related advantages.

SUMMARY OF THE INVENTION

In one embodiment, the invention provides an orally ingestible therapeutic composition containing first and second xanthine compounds along with a cognitive cofactor. The first xanthine compound is caffeine, and the second xanthine compound has the formula:

wherein each of $R^1$, $R^2$ and $R^3$ are independently selected from hydrogen and $C_1$–$C_4$ alkyl, with the proviso that the second xanthine compound is not caffeine.

Cognitive cofactors include biosynthetic precursors to neurotransmitters and neurosteroids, cerebral vasodilators, mineral cofactors, nootropic herbs and essential amino acids. Exemplary cognitive cofactors include ginkgo biloba; glutamic acid and salts thereof, niacin and derivatives containing the niacin nucleus; acetyl-L-carnitine; dimethylaminoethanol (DMAE); L-phenylalanine; choline and salts thereof; glycine and salts thereof, aspartic acid and salts thereof, squalane; squalene; pregnenolone; dehydroepiandrosterone (DHEA); and dehydroepiandrosterone-3-sulphate.

Another aspect of the invention provides a method for enhancing cerebral cortical activity. According to this method, an effective amount of a composition as described above is administered to a subject (such as a warm-blooded animal, including a human subject) in need of enhanced cerebral cortical activity.

In another aspect of this invention, a method is disclosed for enhancing short term memory. According to this method, an effective amount of a composition as described above is administered to a subject in need of enhanced short term memory.

A further aspect of this invention is a method for enhancing weight loss. According to this method, an effective amount of a composition as described above is administered to a subject in need of weight loss.

In still a further aspect of this invention, a method is disclosed for retarding hair loss in a subject in need thereof. According to this method, an effective amount of a composition as described above is administered to a subject experiencing or prone to hair loss.

These and other aspects of this invention will become evident upon reference to the following detailed description.

BRIEF DESCRIPTION OF THE DRAWINGS

FIG. 1A shows the weight loss of subjects who ingested a composition of the present invention, while FIG. 1B shows the weight loss of subjects who ingested caffeine alone, and FIG. 1C shows the weight loss of subjects who ingested a placebo. In each of FIGS. 1A, 1B and 1C, the x-axis represents the number of days each subject was ingesting either inventive composition, caffeine alone or placebo, respectively, while the y-axis indicates the number of pounds which were lost by the average test subject.

DETAILED DESCRIPTION OF THE INVENTION

It has been surprisingly found that administering caffeine ("a first xanthine compound") in conjunction with a xanthine compound other than caffeine ("a second xanthine compound") affords therapeutic effects not observed when an equal weight of caffeine or the second xanthine compound alone is administered. This is particularly true when the second xanthine compound is theophylline. Furthermore, it has been found that administering caffeine, a second xanthine compound and a "cognitive cofactor" provides surprising therapeutic benefits.

Accordingly, the present invention is directed to a composition containing caffeine, a second xanthine compound, and a cognitive cofactor as defined herein. It has been discovered that oral administration of this combination affords beneficial therapeutic effects which may not be achieved by oral administration of any individual component. In addition, as the composition is intended for oral administration, the active ingredients may be formulated with any number of inert carriers and/or diluents to facilitate such administration.

The term "xanthine" as used herein refers to compounds incorporating the xanthine nucleus as shown below, wherein $R^1$, $R^2$, and $R^3$ are independently selected from hydrogen and lower ($C_1$–$C_4$)alkyl.

Exemplary xanthine compounds include xanthine, wherein $R^1$, $R^2$ and $R^3$ are hydrogen; caffeine, also known as trimethylxanthine, where $R^1$, $R^2$ and $R^3$ are each methyl; theophylline, which is also known as 1,3-dimethylxanthine, wherein $R^1$ is hydrogen and $R^2$ and $R^3$ are methyl; and theobromine, also known as 3,7-dimethyl xanthine, wherein $R^1$ and $R^2$ are methyl and $R^3$ is hydrogen.

As used herein, the term "first xanthine compound" means caffeine, and the term "second xanthine compound" refers to xanthine compounds as defined above, excluding caffeine.

Pharmaceutically-acceptable salts, hydrates and solvates of xanthines are also included within the term "xanthines" as used herein. The salt may be an acid- or base- addition salt. Such salts may have at least one negatively charged ion such as chloride, bromide, sulfate, phosphate, $C_{1-15}$carboxylate, methanesulfonate and p-toluenesulfonate, where exemplary $C_{1-15}$carboxylate ions are acetate, glycolate, lactate, pyruvate, malonate, succinate, glutarate, fumarate, malate, tartarate, citrate, ascorbate, maleate, hydroxymaleate, benzoate, hydroxybenzoate, phenylacetate, cinnamate, salicylate and 2-phenoxybenzoate. The salt may have at least one positively charged ion such as lithium, sodium, potassium, beryllium, magnesium, calcium and quaternary ammonium ions, where exemplary quaternary ammonium ions are tetraalkylammonium, and trialkylaralkylammonium ions. A solvate or hydrate may include ethylenediamine.

The inventive composition contains caffeine in addition to at least one other member of the xanthine family which is not caffeine. Thus, the composition may contain caffeine and xanthine, caffeine and theophylline, caffeine and theobromine or caffeine, theophylline and xanthine, to name a few representative possibilities. In one embodiment, the composition contains caffeine and theophylline as the only active ingredients from the xanthines as defined above. The ratio of the weight of caffeine to the total weight of the other members of the xanthine family within the composition typically ranges from 1:3 to 3:1, and preferably ranges from 1:2 to 2:1.

Xanthines are commercially available in pure from, and, as such, may be used in preparing compositions of the invention. For example, caffeine and theophylline are each available in 99% purity from Aldrich Chemical Company (Milwaukee, Wis.), and may also be obtained from Sigma Chemical Company (St. Louis, Mo.).

Both caffeine and theophylline are known to have desirable effects on the mammalian body. Caffeine dilates coronary arteries and bronchioles in the lungs. In time, it also induces cerebral vasoconstriction and is a powerful neurostimulant. Theophylline increases bronchial dilation significantly, thereby enhancing the transportation of oxygen into cells and carbon dioxide out of the body, and is a low grade cortical neurostimulant. Caffeine, however, is known to significantly enhance mental performance and to prolong a wakeful state. Both caffeine and theophylline are known to enhance physical performance.

In addition to caffeine and a second (non-caffeine) xanthine, the inventive composition contains one or more cognitive cofactors. As used herein, a cognitive cofactor ameliorates the diffuse chronic depolarization and subsequent cortical depression commonly associated with stimulants alone. Exemplary cognitive cofactors include, without limitation, biosynthetic precursors to neurotransmitters or neurosteroids, cerebral vasodilators, minerals, nootropic herbs, and essential amino acids.

The biosynthetic precursor of a neurotransmitter is a compound which, upon ingestion by a subject, is converted in vivo into a neurotransmitter, while a biosynthetic precursor of a neurosteroid is a compound which, upon ingestion by the subject, is converted in vivo into a neurosteroid. Biosynthetic precursors of both neurotransmitters and neurosteroids are well known in the art.

The following are exemplary cognitive cofactors according to the invention: ginkgo biloba; niacin and derivatives containing the niacin nucleus; acetyl-L-carnitine; dimethylaminoethanol (DMAE); choline including esters and salts thereof, amino acids including salts and esters thereof, such as L-phenylalanine, glutamic acid, glycine, and aspartic acid; squalane; squalene; pregnenolone; dehydroepiandrosterone (DHEA); and dehydroeplandrosterone-3-sulphate. All of these biosynthetic precursors can be acquired from Sigma Chemical Company (St. Louis, Mo.).

A description of some of the above precursors follows:

Ginkgo biloba is a nootropic herb. It has been found to significantly increase cerebral circulation, enhance mental alertness, and increase the production of ATP in the brain. It also improves the ability of the brain to metabolize glucose. It is a powerful antioxidant and cerebral vasodilator.

Niacin and derivatives thereof include compounds that contain the niacin nucleus, which is shown below:

Niacin and derivatives thereof include, but are not limited to, niacin, xanthinol nicotinate, methyl nicotinate, tocopheral nicotinate, and inositol hexanicotinate. Xanthinol nicotinate is a preferred niacin derivative and a preferred cognitive cofactor according to the invention. Xanthinol nicotinate is known to be a potent cerebral vasodilator of significant specificity, has been used for many years to lower serum cholesterol, and has been shown to dramatically enhance cerebral blood flow. On the basis of in vivo testing, it is also known that once inside brain cells, xanthinol nicotinate will increase glucose metabolism and correspondingly increase AIP. Xanthinol nicotinate does not generally cause flushing.

Acetyl-L-carnitine is related to choline compounds both clinically and chemically. Acetyl-L-carnitine protects the brain from the effects of aging. It has been definitively shown to decrease the buildup of lipofuscin pigments which are found in the brains of aged mammals. A buildup of these fatty deposits in nerve cells is associated with reduction of cognitive powers and a decrease in the rate of depolarization of nerve cells. Acetyl-L-carnitine increases brain levels of choline-acetyl-transferase and acetylcholine, a vital neurotransmitter.

Dimethylaminoethanol, or DMAE, is normally present in small amounts in mammalian brains. DMAE is known for its ability to elevate mood, enhance memory, increase intelligence, and increase the rate at which learning is accomplished. DMAE may take some time to have its effect noticed when taken alone. DMAE works by accelerating the brain synthesis of the neurotransmitter acetylcholine. In the present composition, DMAE acts synergistically to dramatically enhance the effects of the xanthine stimulants.

Choline esters and salts as present in compositions of the present invention are biosynthetic precursors to acetyl choline. A preferred choline salt is choline bitartrate, which is a phospholipid that is the immediate biosynthetic precursor of acetylcholine. Choline is known for its ability to improve memory by increasing the amount of acetylcholine in the brain. Choline bitartrate is a preferred form of choline because of its water solubility, which makes it more readily absorbable on the basis of oral administration.

Glutamic acid esters and salts, as used herein, includes pyroglutamate and arginine pyroglutamate. Pyroglutamate is a glutamic acid compound that is present in very large amounts in the human brain, cerebral spinal fluid, and blood. Pyroglutamate is known to have a number of remarkable cognitive enhancing effects. Studies have shown that pyroglutamate will effectively treat alcohol-induced memory deficits in humans. It has been shown that pyroglutamate can be very effectively transformed in the brain into the neurotransmitter glutamine. Arginine pyroglutamate has been found to not only enhance cognition, but is also an excellent growth hormone releasing factor because it is carried far more efficiently across the blood brain barrier than arginine alone. Other glutamic acid compounds are also efficacious as neurotransmitter precursors.

Aspartic acid and esters and salts thereof includes, without limitation, the sodium and potassium salts of aspartic acid. Potassium aspartate is a preferred aspartic acid salt, which may be used to enhance the intracellular ionic balance in the central nervous system which may otherwise be depleted by various stimulants.

Squalane and squalene are immediate biosynthetic precursors of all steroid molecules, including neurosteroids, and can be converted as needed to pregnenolone and/or other steroids. Pregnenolone is a neurosteroid which is known to enhance memory function. It has been conclusively shown to decrease GABA (gamma-amino-butyric acid) activity and thereby enhance wakefulness. Dehydroepiandrosterone and dehydroeplandrosterone-3-sulphate are related neurosteroids that are known to stabilize cell membranes. In particular, they are known to affect astrocytes and the splingomyelin sheath.

In the inventive composition, the ratio of the total weight of caffeine and other xanthine compounds to the total weight of the cognitive cofactors typically ranges from 1:3 to 3:1, and preferably ranges from 1:2 to 2:1.

In addition to the above-identified ingredients, the composition may contain optional ingredients. One optional ingredient is a stimulant, which is not one of the above-mentioned ingredients. In general, materials known to have a stimulatory effect are well known in the art, and any of these materials may be present in the composition of the invention. An exemplary stimulant is phenethylamine.

The active ingredients in the inventive composition can be administered as a mixture thereof, or in combination with one or more pharmaceutically acceptable inert materials, binders, carriers or excipients, collectively referred to as adjuvants. Thus, the composition may contain binders such as microcrystalline cellulose, gum tragacanth or gelatin; excipients such as starch or lactose; carriers such as sucrose, kaolin, glycerin, starch dextrins, sodium alginate, carboxymethylcellulose and ethyl cellulose; disintegrating agents such as alginic acid, Primogel, corn starch and the like; lubricants such as magnesium stearate or Sterotex; and glidants such as colloidal silicon dioxide. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. Materials used in preparing these various compositions should be pharmaceutically pure and non-toxic in the amounts used. See, e.g., Remington's Pharmaceutical Sciences, 18th Edition, Mack Publishing Co. (1990).

The composition may be formulated as an easily swallowed form, such as a pill, tablet or capsule. Thus, the active ingredients may be enclosed in gelatin capsules or compressed into tablets. The composition may be readily mixed with other ingestible material, in which case a powdered form may be preferred. The composition may be in the form of a wafer or chewing gum. The composition may be a liquid, such as an elixer, suspension or syrup. In any case, the composition may be formulated to have a pleasant taste, or it may be coated so that it has essentially no taste. For example, sweetening agents such as sucrose or saccharin may be added or a flavoring agent such as peppermint, methyl salicylate or orange flavoring. Coloring agents, e.g., dyes, may also be present. Therefore, the invention provides a pharmaceutical or veterinary composition comprising an effective amount of active ingredients as described herein, in association with a carrier.

The invention provides, in one embodiment, a therapeutic composition for oral administration which includes caffeine, a second xanthine other than caffeine, and a cognitive cofactor as defined above. Thus, the invention provides compositions for oral administration which include caffeine, a xanthine compound other than caffeine and ginkgo biloba; caffeine, a xanthine compound other than caffeine, and glutamic acid or ester or salt thereof, caffeine, a xanthine compound other than caffeine, and niacin or derivative thereof, caffeine, a xanthine compound other than caffeine and acetyl-L-carnitine; caffeine, a xanthine compound other than caffeine, and dimethylaminoethanol; caffeine, a xanthine compound other than caffeine, and an amino acid or ester or salt thereof; caffeine, a xanthine compound other than caffeine, and L-phenylalanine; caffeine, a xanthine compound other than caffeine, and choline or a salt thereof, caffeine, a xanthine compound other than caffeine, and glycine or ester or salt thereof, caffeine, a xanthine compound other than caffeine, and aspartic acid or ester or salt thereof, caffeine, a xanthine compound other than caffeine, and squalane; caffeine, a xanthine compound other than caffeine, and squalene; caffeine, a xanthine compound other than caffeine, and pregnenolone; caffeine, a xanthine compound other than caffeine, and dehydroepiandrosterone; caffeine, a xanthine compound other than caffeine, and dehydroepiandrosterone-3-sulfate. In one embodiment, the xanthine compound other than caffeine is theophylline. In another embodiment, the niacin or derivative thereof is xanthinol nicotinate. In still another embodiment, the glutamic acid or ester or salt thereof is pyroglutamate. In yet a further embodiment of the invention, the afore-listed compositions contain only the mentioned compounds as active ingredients.

The inventive composition may be administered to achieve a variety of beneficial effects. Thus, the composition may serve as a stimulant, to increase cerebral cortical activity, to elevate mood, to enhance short-term memory, to provide increases in musculature and athletic performance, decreases in appetite, and a decrease in hair loss. These beneficial effects are discussed further below.

It has been surprisingly found that the inventive compositions provides a sustained and noticeable stimulant effect far beyond that typically observed upon ingestion of an equivalent amount of caffeine or second xanthine compound alone. The invention is therefore also directed to a method of employing the composition of the invention to enhance cerebral cortical activity and thereby provide a stimulatory effect. Thus, the invention provides a method for enhancing cerebral cortical activity in a subject in need thereof A "subject in need thereof" may be a warm-blooded animal who has been diagnosed to have attention deficiency disease. According to the method, an effective amount of a composition as described above is administered to a subject in need of enhanced cerebral cortical activity. Furthermore, the inventive composition affords this stimulant effect with an amelioration of the diffuse chronic depolarization and subsequent cortical depression commonly associated with stimulants alone. Accordingly, methods for enhancing cerebral cortical activity while ameliorating the diffuse chronic depolarization and subsequent cortical depression commonly associated with stimulants alone is provided by the present invention.

It has also been surprisingly found that the inventive composition may afford substantial enhancements in short term memory as compared with caffeine alone. The invention is therefore also directed to a method of employing the composition of the invention to aid short term memory recall. Thus, the invention provides a method for enhancing the short term memory a subject in need thereof, comprising oral administration to the subject of an effective amount of a composition of the invention as described above.

In a preferred embodiment, the inventive composition contains a biosynthetic precursor to a neurosteroid. When the composition contains a biosynthetic precursor to a neurosteroid, it is particularly preferred to administer such a composition to a subject in need of increases in muscular development and athletic performance, decreases in appetite and/or decreases in hair loss. Thus, subjects who are predisposed to alopecia may be in need of oral administration of the composition of the present invention, in order to reduce hair loss.

It has also been surprisingly found that the inventive composition causes a significant reduction in the appetite of an overweight person who consumes the composition. Overweight persons who consume the inventive composition experience weight loss because their caloric consumption decreases as their interest in food is reduced. The inventive composition is therefore useful for weight reduction and longterm weight management. Thus, the invention provides a method for achieving weight reduction comprising administering to a subject in need thereof an effective amount of the composition of the invention as described above.

The stimulant aspect of the present invention may be enhanced by increasing the amount of phenylalanine present in the inventive composition. Concurrently, the anorectic effect of such a composition (having a high phenylalanine content) may also be substantially augmented. In conjunction with a xanthine compound according to the present invention, a composition with an elevated phenylalanine content provides a notable increase in weight loss, and when combined with the components of the composition of Formulation IV (below), the amount of weight lost may be increased. The composition disclosed in Formulation III is exemplary of compositions of the invention having an elevated phenylalanine content. The compositions of Formulations III and IV may be administered orally in a variety of different forms, including, but not limited to, capsules, tablets, powder, and syrups.

It has also been surprisingly found that the inventive composition causes a dramatic reduction in hair loss in subjects predisposed to androgenetic alopecia. The invention is therefore also directed to a method of employing the composition of the invention to retard hair loss. Thus, the invention provides a method for retarding hair loss from a subject experiencing hair loss and/or predisposed to androgenetic alopecia, comprising oral administration to the subject of an effective amount of a composition of the invention as described above.

Thus, the invention extends to the use of a composition including caffeine, a second (non-caffeine) xanthine, and a biosynthetic precursor to neurotransmitter or neurosteroid, for the manufacture of a medicament for use in therapy, including the effects described above (i.e., retarding hair loss, effecting weight reduction, enhancing short term memory and increasing cerebral cortical activity).

The term "effective amount" refers to an amount which is effective, upon single or multiple dose administration to the subject, in providing one or more effects as described herein. In determining the effective amount or dose, a number of factors are considered by the attending diagnostician, including, but not limited to: the species of mammal; its size, age, and general health; the specific goal desired; the severity of the problem being experienced by the subject; the responsiveness of the individual subject to the treatment; the particular composition administered; the bioavailability characteristics of the preparation administered; the dose regimen selected; the use of concomitant medication; and other relevant circumstances.

In general, to achieve the beneficial results described above, a person in need thereof may be administered active ingredients in an amount ranging from about 0.1 milligram per kilogram of body weight per day (mg/kg/day) to about 100 mg/kg/day. For the average person, a typical daily dosage is an amount ranging from 10 mg to 500 mg of caffeine in combination with a second xanthine compound (not caffeine) in an amount ranging from 1 mg to 1000 mg. The cognitive cofactor is present in a typical dosage in an amount ranging from 1 mg to 1000 mg. Preferred compositions contain from 50 mg to 250 mg caffeine, from 10 to 500 mg of the second xanthine compound, and from 10 mg to 500 mg of the cognitive cofactor.

The compositions formulated for oral administration should generally contain at least about 4% of the active ingredients as identified above, but that amount may be varied up to 100% of the weight of the unit, if desired. The amount of the active ingredients present in orally-administered compositions is such that a suitable dosage will be obtained. Preferred compositions and preparations according to the present invention are prepared so that an oral dosage unit form contains between 5.0–300 milligrams of the active ingredients as identified herein.

As used herein, the term "subject" refers to a warm-blooded animal such as a mammal which is need of treatment. It is understood that guinea pigs, dogs, cats, rats, mice, horses, cattle, sheep, and humans are examples of animals within the scope of the meaning of the term.

The following examples are provided for purposes of illustration, not limitation.

EXAMPLES

Example 1

Representative Compositions

The following Formulations I and II are representative compositions of the present invention formulated for oral administration. The compositions may be formulated by mixing the indicated ingredients to form a "unit" for oral administration, according to the weights, in milligrams, shown, The various ingredients may be obtained from, e.g., Sigma Chemical Company (St. Louis, Mo.).

| Ingredient | mg/unit |
|---|---|
| Formulation I | |
| Gingko A | 5.0 |
| Theophylline | 25.0 |
| Caffeine | 27.5 |
| Green tea | 84.0 |
| L-pyroglutamate | 75.0 |
| Xanthinol nicotinate | 38.0 |
| N-Acetyl-L-carnitine | 7.5 |
| Choline bitartrate | 122.0 |
| DMAE bitartrate | 60.0 |
| Magnesium glycinate | 25.0 |
| Potassium aspartate 221% | 50.0 |
| L-phenylalanine | 50.0 |
| Formulation II | |
| Gingo A | 5.0 |
| Theophylline | 25.0 |
| Caffeine | 27.5 |
| Green tea | 84.0 |
| L-Pyroglutamate | 75.0 |
| Xanthinol nicotinate | 38.0 |
| N-Acetyl-L-carnitine | 7.5 |
| Choline | 122.0 |
| DMAE | 50.0 |
| Magnesium glycinate | 25.0 |
| Potassium Aspartate 21% | 50.0 |
| L-phenylalanine | 50.0 |
| Pregnenolone | 50.0 |
| DHEA | 25.0 |
| Squalane | 100.0 |

Example 2

Stimulant Effect

The following example illustrates the administration of a representative composition of the present invention to achieve stimulant effects.

Five subjects were tested over a period of three days. On each day, each subject randomly consumed a composition which was either a placebo, a 180 mg dosage of caffeine, or Formulation I of Example 1, such that over the three-day period, each subject had consumed each composition one time. Both prior to and after consuming the composition, each subject played a video game of skill called Pilot Wing™ made by Nintendo™.

The subjects consistently received higher scores after consuming Formulation I, then they did after consuming placebo or caffeine alone (subjects received higher scores after consuming the caffeine, compared to consuming the placebo). No adverse side effects were observed.

Example 3

Short-Term Memory Effect

The following example illustrates the administration of a representative composition of the present invention to achieve short-term memory enhancement.

Five subjects were given a standard short-term memory test on three consecutive days after being administered a composition which was either two units of Formulation I from Example 1, 180 mg of caffeine, or a placebo. The test consisted of an examiner reading a series of numbers to the subject and the subject subsequently being asked to repeat said numbers backward. In all cases, the test was initiated 30 minutes after ingestion of the composition. In all cases, a subject receiving Formulation I performed better than when he or she received either caffeine or the placebo. Three of the subjects receiving Formulation I were able to repeat up to eight digits backwards without error, while those same subjects could not repeat this accomplishment after administration of either caffeine alone or the placebo. No adverse effects were seen.

Example 4

Weight Loss

The following example illustrates the administration of a representative composition of the present invention to achieve weight loss.

Figure 1A:
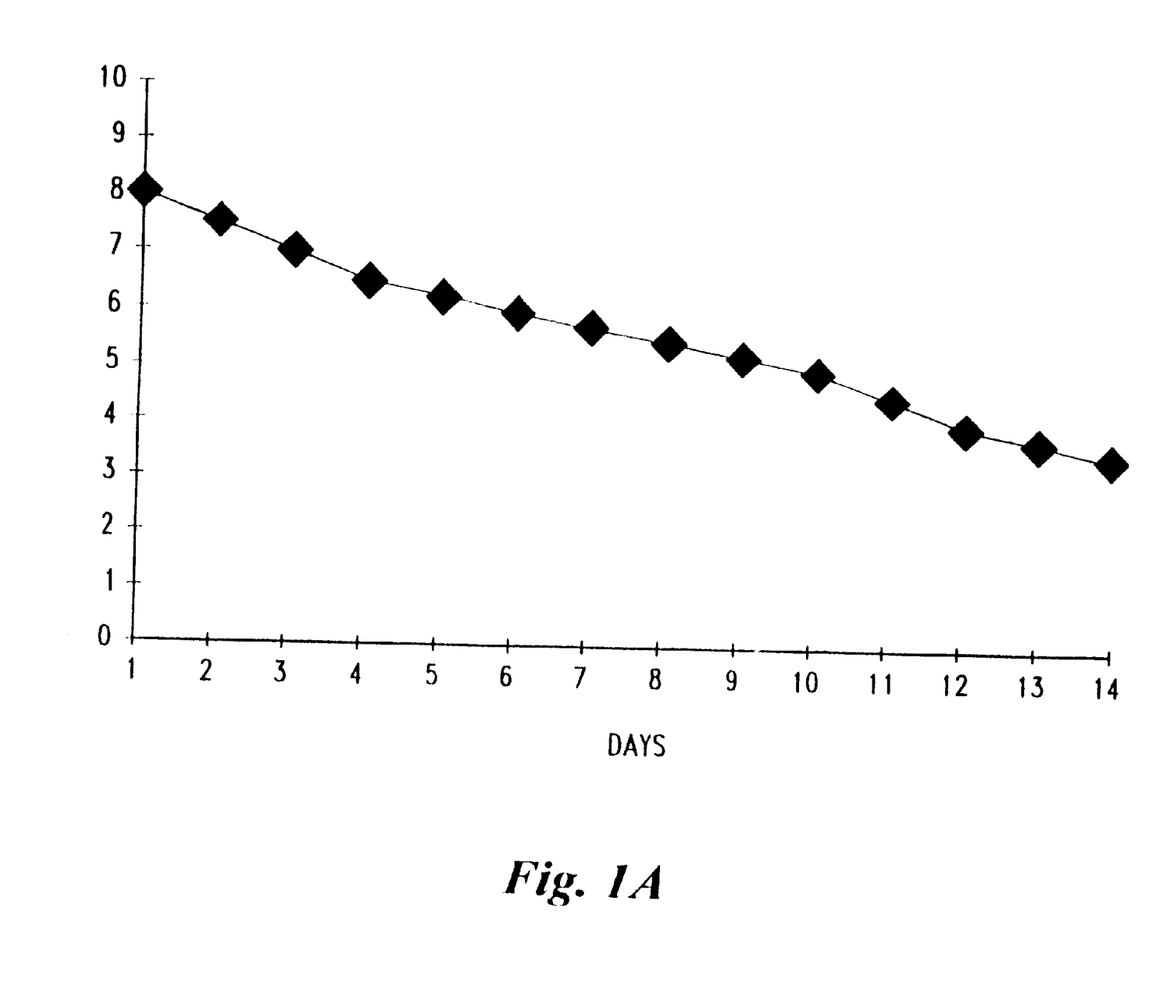
FIGS. 1A–1C show the results of a weight loss experiment as described herein.
Figure 1B:
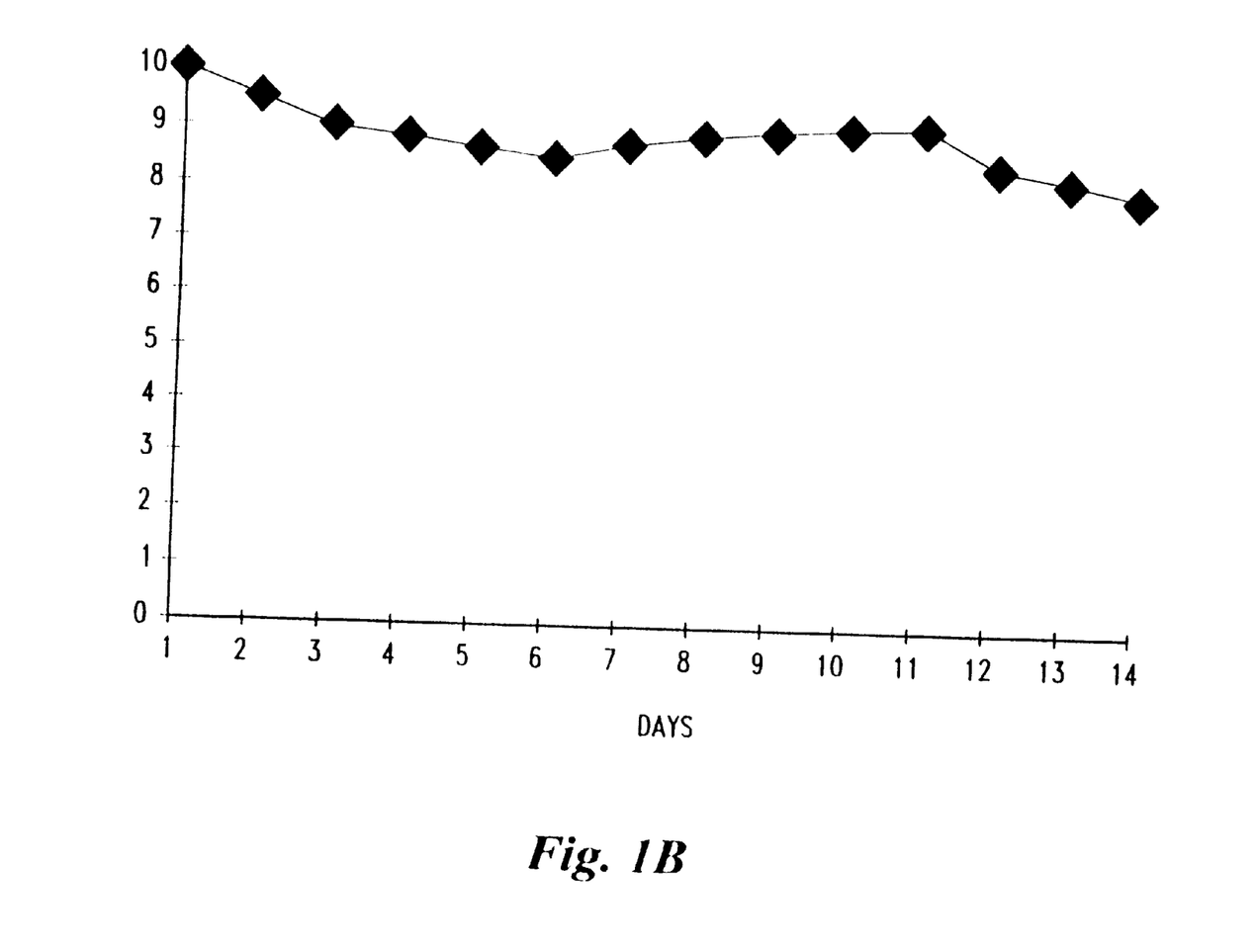
Figure 1C:
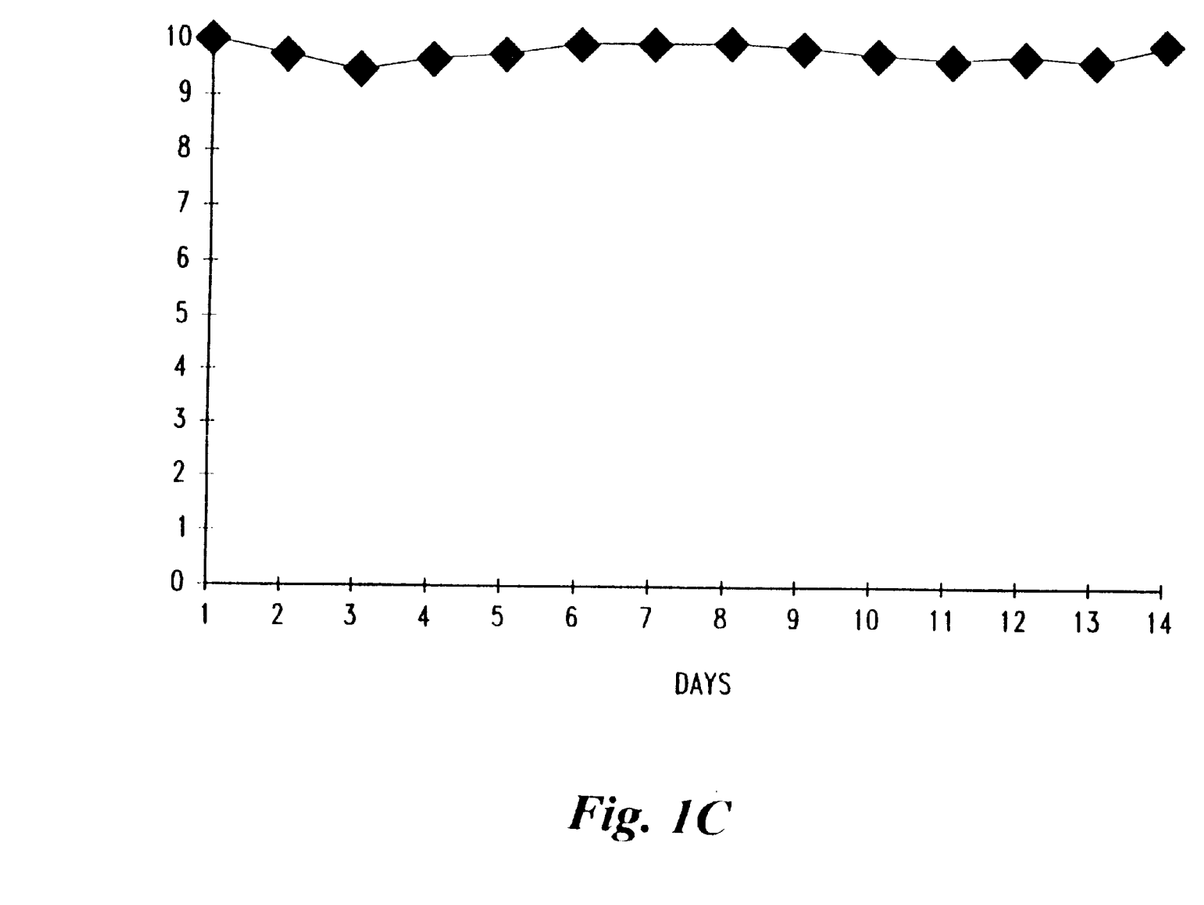

On a daily basis over a two week time span, ten overweight subjects received Formulation I from Example 1, five different overweight subjects received 180 mg capsules of caffeine, and another five overweight subjects received the placebo. Weights were averaged and weight loss was charted every three days in all groups. As noted in the graphs, subjects consuming Formulation I lost an average of 3½ pounds in two weeks. This result was not matched by those subjects who consumed caffeine or the placebo. No adverse effects were observed.

These results are shown in FIG. 1. In FIG. 1A, the weight loss of subjects receiving Formulation I is shown, while in FIG. 1B, the weight loss of subjects receiving caffeine alone is shown, while in FIG. 1C the weight loss of subjects receiving the placebo is shown. Subjects receiving the placebo showed no weight loss, while subjects receiving Formulation I showed the greatest weight loss.

Example 5

Hair Loss

The following example illustrates the administration of a representative composition of the present invention to achieve a reduction in hair loss.

Five subjects with persistent chronic hair loss were given Formulation I from Example 1 on a daily basis over a three week time span. They were asked to count hairs lost each day, and this data was averaged each week to determine the average hair loss per day, per week. The results of this experiment were as follows:

|  |  | Hairs Lost/Day |
|---|---|---|
| Subject 1 | Week 1 | 226 |
|  | Week 3 | 130 |
| Subject 2 | Beginning | 168 |
|  | End (3 Weeks) | 76 |
| Subject 3 | Beginning | 345 |
|  | End (3 weeks) | 82 |
| Subject 4 | Beginning | 179 |
|  | End (3 weeks) | 58 |
| Subject 5 | Beginning | 246 |
|  | End (3 weeks) | 66 |

Example 6

Stimulant Effect

Five individuals were given 3 capsules of the composition set forth as Formulation III, below, at 11 p.m. They were then told to note when they felt the need to sleep. One week later they were given 3 capsules of placebo and asked to note when they felt the need to sleep. The total time between the taking of the capsules and the initiation of sleep was added up and divided by the number of subjects. In the placebo group the average time was 1 hr., 38 min. In the group receiving the composition of Formulation III, the average time was 3 hr., 26 min. This demonstrates that a composition of the invention, namely Formulation III, has a stimulant effect far in excess of placebo control.

| Formulation III | |
|---|---|
| Amount (mg) | Ingredient: |
| 600 | L-Phenylalanine |
| 200 | DMAE bitartrate pwd. |
| 180 | Caffeine |
| 150 | Choline Bitartrate |
| 125 | Vitamin C |
| 120 | Theofylline |
| 112.5 | L-Pyroglutamate |
| 82 | Inulin |
| 75 | Green Tea Powder |
| 57 | Xanthinol Nicotinate |
| 50 | D Calcium Pantothenate |
| 20 | Potassium Aspartate 23% |
| 15 | Vitamin B6 |
| 15 | Magnesium Stearate |
| 4 | Vitamin B2 |
| 4 | Copper Chloride |
| 3.9 | Aulterra Powder |
| 3 | Vanadyl Sulfate |
| 2 | Vitamin B1 |
| 0.4 | Chromium Proteinate |
| 0.05 | Vitamin B12 |
| 1818.85 | Total |

Example 7

Weight Loss Effect

Figure 2:
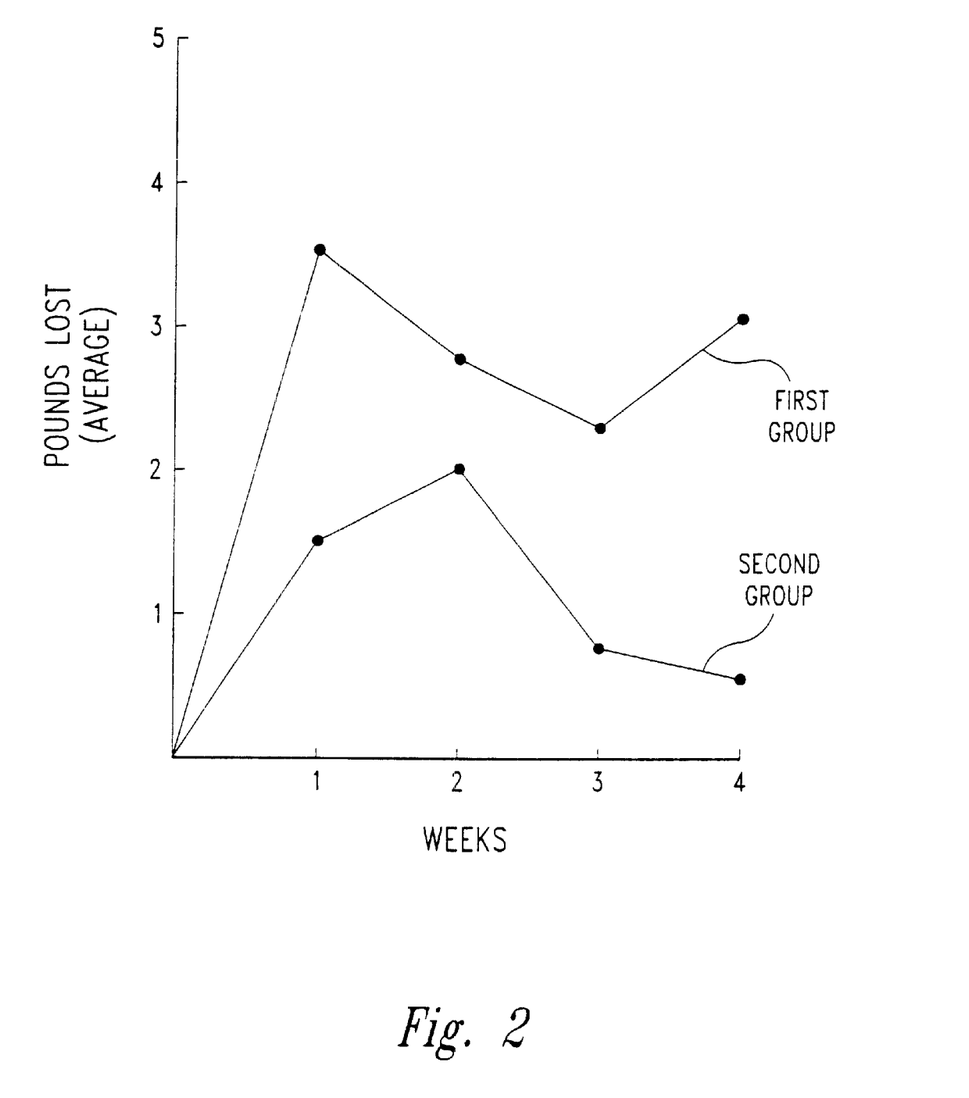
FIG. 2 is a graph showing weight loss (in pounds) of a group of individuals administered a representative composition of this invention.

A cohort of 10 individuals ("the first group") was administered 3 capsules of the composition of Formulation III (see Example 6) in the morning along with 2 capsules of the composition of Formulation IV (below). In the afternoon at 2 p.m., the subjects were administered 1 capsule of the composition of Formulation III and 2 capsules of the composition of Formulation IV. The weight loss was then averaged on a weekly basis for 4 weeks. Another group of 10 individuals ("the second group") was told to eat a 1600 cal./day diet. They too were weighed on a weekly basis and the total amount of weight lost was averaged on a weekly basis for 4 weeks. In all cases individuals in the first group lost more weight than individuals in the second group. The results are noted in FIG. 2. The anorectic effect of the combination of the compositions of Formulations III and IV was substantially more effective than diet alone.

| Formulation IV | |
|---|---|
| Amount (mg) | Ingredient: |
| 450 | Inulin Cosucra |
| 200 | L-Tyrosine |

| Formulation IV (continued) | |
|---|---|
| Amount (mg) | Ingredient: |
| 200 | Di Calcium Phosphate |
| 75 | L-Methionine |
| 50 | Panax Ginseng |
| 50 | Astragalus |
| 50 | Ethyl Vanillin |
| 20 | Ascorbyl Palmitate |
| 15 | Chamomile |
| 15 | Licorice Root |
| 15 | Uva Ursi |
| 4 | Copper Chloride |
| 1144 | Total |

Although other nootropic substances could be used, these were found to be optimal for the present composition. However other substances that may be of value include, but are not limited to: piracetam, centrophenoxine, hydergine and related ergot-based based alkaloids and other vasoactive compounds, which include, but are not limited to, Vinpocetine, Papaverine, and related alkaloids. Various neurosteroids were also found to be useful in the composition. These steroids include DHEA (dehydroepiandrosterone), dehydroepiandrosterone-3-sulfate, and pregnenolone. Steroid precursors were also considered to be of some value and included squalane and squalene.

From the foregoing, it will be appreciated that, although specific embodiments of this invention have been described herein for the purposes of illustration, various modifications may be made without departing from the spirit and scope of the invention. Accordingly, the invention is not limited except by the appended claims.

What is claimed is:

1. A method for enhancing short term memory of a subject in need thereof, comprising orally administering to the subject an effective amount of a composition comprising caffeine, theophylline, and a cognitive cofactor wherein the caffeine ranges between 10 and 20% by weight of the composition, the theophylline ranges between 5 and 10% by weight of the composition, and the cognitive cofactors are gingko biloba—A, which ranges between 0 and 1% by weight of the composition, L-pyroglutamate, which ranges between 5 and 10% by weight of the composition, Xanthinol nicotinate, which ranges between 5 and 10% by weight of the composition, N-Acetyl-L-carnitine, which ranges between 0 and 1% by weight of the composition, Choline Bitartrate, which ranges between 15 and 25% by weight of the composition, DMAE, which ranges between 15 and 20% by weight of the composition, Magnesium glycinate, which ranges between 0 and 5% by weight of the composition, Potassium aspartate (21%), which ranges between 5 and 10% by weight of the composition, and L-phenylalanine, which ranges between 10 and 20% by weight of the composition.

2. The method of claim 1 wherein
the caffeine is approximately 15.4% by weight of the composition,
the theophylline is approximately 7.0% by weight of the composition, and
the cognitive cofactors are
- gingko biloba—A at approximately 0.35% by weight of the composition,
- L-pyroglutamate at approximately 7.0% by weight of the composition,
- Xanthinol nicotinate at approximately 7.0% by weight of the composition,
- N-Acetyl-L-carnitine at approximately 0.52% by weight of the composition,
- Choline Bitartrate at approximately 21.0% by weight of the composition,
- DMAE at approximately 17.5% by weight of the composition,
- Magnesium glycinate at approximately 3.5% by weight of the composition,
- Potassium aspartate (21%) at approximately 7.0% by weight of the composition, and
- L-phenylalanine at approximately 14.0% by weight of the composition.

3. A method for enhancing weight loss of a subject in need thereof, comprising caffeine, theophylline, and a cognitive cofactor wherein
the caffeine ranges between 10 and 20% by weight of the composition,
the theophylline ranges between 5 and 10% by weight of the composition, and
the cognitive cofactors are
- gingko biloba—A, which ranges between 0 and 1% by weight of the composition,
- L-pyroglutamate, which ranges between 5 and 10% by weight of the composition,
- Xanthinol nicotinate, which ranges between 5 and 10% by weight of the composition,
- N-Acetyl-L-carnitine, which ranges between 0 and 1% by weight of the composition,
- Choline Bitartrate, which ranges between 15 and 25% by weight of the composition,
- DMAE, which ranges between 10 and 20% by weight of the composition,
- Magnesium glycinate, which ranges between 0 and 5% by weight of the composition,
- Potassium aspartate (21%), which ranges between 0 and 10% by weight of the composition,
- Chromium arginate, which ranges between 10 and 20% by weight of the composition, and
- L-phenylalanine, which ranges between 10 and 20% by weight of the composition.

4. The method of claim 3 wherein
the caffeine is approximately 16% by weight of the composition,
the theophylline is approximately 8.0% by weight of the composition, and
the cognitive cofactors are
- gingko biloba—A at approximately 0.36% by weight of the composition,
- L-pyroglutamate at approximately 7.3% by weight of the composition,
- Xanthinol nicotinate at approximately 6.2% by weight of the composition,
- N-Acetyl-L-carnitine at approximately 0.55% by weight of the composition,
- Choline Bitartrate at approximately 8.9% by weight of the composition,
- DMAE at approximately 14.6% by weight of the composition,
- Magnesium glycinate at approximately 1.8% by weight of the composition,
- Potassium aspartate (21%) at approximately 3.6% by weight of the composition,
- Chromium arginate at approximately 14.6% by weight of the composition, and
- L-phenylalanine at approximately 18.2% by weight of the composition.

5. A method for enhancing short term memory of a subject in need thereof, comprising orally administering to the subject an effective amount of a composition comprising caffeine, theophylline, and a cognitive cofactor wherein
the caffeine ranges between 10 and 20% by weight of the composition,
the theophylline ranges between 5 and 10% by weight of the composition, and
the cognitive cofactors are
- gingko biloba—A, which ranges between 0 and 2% by weight of the composition,
- L-pyroglutamate, which ranges between 5 and 10% by weight of the composition,
- Xanthinol nicotinate, which ranges between 5 and 10% by weight of the composition,
- N-Acetyl-L-carnitine, which ranges between 0 and 2% by weight of the composition,
- Choline Bitartrate, which ranges between 10 and 25% by weight of the composition,
- DMAE, which ranges between 15 and 25% by weight of the composition,
- Magnesium glycinate, which ranges between 0 and 5% by weight of the composition,
- Potassium aspartate (21%), which ranges between 0 and 5% by weight of the composition, and
- L-phenylalanine, which ranges between 10 and 20% by weight of the composition.

6. The method of claim 5 wherein
the caffeine is approximately 17.7% by weight of the composition,
the theophylline is approximately 8.8% by weight of the composition, and
the cognitive cofactors are
- gingko biloba—A at approximately 1.3% by weight of the composition,
- L-pyroglutamate at approximately 8.7% by weight of the composition,
- Xanthinol nicotinate at approximately 8.8% by weight of the composition,
- N-Acetyl-L-carnitine at approximately 1.3% by weight of the composition,
- Choline Bitartrate at approximately 11.1% by weight of the composition,
- DMAE at approximately 22.1% by weight of the composition,
- Magnesium glycinate at approximately 0.18% by weight of the composition,
- Potassium aspartate (21%) at approximately 4.4% by weight of the composition, and
- L-phenylalanine at approximately 13.3% by weight of the composition.

* * * * *